(12) United States Patent
Lynch et al.

(10) Patent No.: US 8,008,286 B2
(45) Date of Patent: *Aug. 30, 2011

(54) METHOD FOR TREATMENT OF NEUROPATHIC PAIN

(75) Inventors: Kevin R. Lynch, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/179,816

(22) Filed: Jul. 25, 2008

(65) Prior Publication Data

US 2009/0062238 A1  Mar. 5, 2009

Related U.S. Application Data

(63) Continuation of application No. PCT/US2007/002422, filed on Jan. 29, 2007.

(60) Provisional application No. 60/762,589, filed on Jan. 27, 2006.

(51) Int. Cl.
*A01N 43/00* (2006.01)
*A61K 31/33* (2006.01)

(52) U.S. Cl. ........ 514/183; 514/114; 514/647; 564/307; 564/15

(58) Field of Classification Search .................. 514/114, 514/647; 564/307, 15
See application file for complete search history.

(56) References Cited

U.S. PATENT DOCUMENTS

| | | |
|---|---|---|
| 3,153,092 A | 10/1964 | Burger |
| 4,939,130 A | 7/1990 | Jaeggi et al. |
| 5,405,988 A | 4/1995 | Klar et al. |
| 6,069,251 A | 5/2000 | Thurkauf et al. |
| 6,875,757 B2 | 4/2005 | Miller et al. |
| 7,060,697 B2 | 6/2006 | Marsilje et al. |
| 7,064,217 B2 | 6/2006 | Macdonald et al. |
| 7,241,790 B2 | 7/2007 | Lynch et al. |
| 2004/0224941 A1 | 11/2004 | Seko et al. |
| 2005/0023386 A1 | 2/2005 | Nishi et al. |
| 2005/0032744 A1 | 2/2005 | Michaelis et al. |
| 2005/0222422 A1* | 10/2005 | Lynch et al. ................. 548/112 |
| 2006/0122181 A1 | 6/2006 | Ikemoto et al. |
| 2006/0135786 A1 | 6/2006 | Saha et al. |
| 2006/0211656 A1 | 9/2006 | Albert et al. |
| 2006/0223866 A1 | 10/2006 | Evindar et al. |
| 2007/0088002 A1 | 4/2007 | Lynch et al. |
| 2007/0191313 A1 | 8/2007 | Beard et al. |
| 2008/0249070 A1 | 10/2008 | Lynch et al. |
| 2009/0042955 A1 | 2/2009 | Lynch et al. |
| 2009/0105315 A1 | 4/2009 | Lynch et al. |
| 2009/0137531 A1 | 5/2009 | Lynch et al. |
| 2009/0253759 A1 | 10/2009 | Lynch et al. |
| 2009/0253760 A1 | 10/2009 | Lynch et al. |
| 2009/0253761 A1 | 10/2009 | Lynch et al. |

FOREIGN PATENT DOCUMENTS

| | | |
|---|---|---|
| DE | 1 056 139 | 4/1959 |
| DE | 3 544 373 A1 | 6/1987 |
| EP | 1 553 091 A1 | 7/2005 |
| EP | 1 602 660 A1 | 12/2005 |
| GB | 950388 | 2/1964 |
| JP | 1994 135935 | 5/1994 |
| JP | 1994 135936 | 5/1994 |
| JP | 2002 316985 | 10/2002 |
| JP | 2004 307442 | 4/2004 |
| WO | WO 99/35259 | 7/1999 |
| WO | WO 01/60819 A1 | 8/2001 |
| WO | WO 01/71022 A2 | 9/2001 |
| WO | WO 02/076995 A2 | 10/2002 |
| WO | WO 02/092068 A1 | 11/2002 |
| WO | WO 03/059880 A1 | 7/2003 |
| WO | WO 03/061567 A2 | 7/2003 |
| WO | WO2004/010987 A2 | 2/2004 |
| WO | WO 2004010949 A2 * | 2/2004 |
| WO | WO 2004/017917 A2 | 3/2004 |
| WO | WO 2004/024673 A1 | 3/2004 |
| WO | WO 2004/028521 A2 | 4/2004 |
| WO | WO 2004/047743 A2 | 6/2004 |
| WO | WO 2004/096752 A1 | 11/2004 |
| WO | WO 2004/096757 A1 | 11/2004 |
| WO | WO 2004/103279 A2 | 12/2004 |
| WO | WO 2004/103306 A2 | 12/2004 |
| WO | WO 2005/032465 A2 | 4/2005 |
| WO | WO 2005/118523 A1 | 12/2005 |
| WO | WO 2006/001463 A1 | 1/2006 |
| WO | WO 2006/020951 A1 | 2/2006 |
| WO | WO 2007/085451 A2 | 8/2007 |
| WO | WO 2007/086001 A2 | 8/2007 |
| WO | WO 2007/091396 A1 | 8/2007 |
| WO | WO 2009/023854 A1 | 2/2009 |
| WO | WO 2009/043013 A2 | 4/2009 |
| WO | WO 2009/146112 A2 | 12/2009 |

OTHER PUBLICATIONS

Dworkin et al. Advances in Neuropathic Pain, Diagnosis, Mechanism and Treatment Recommendations, Arch Neurol/vol. 60, Nov. 2003.*
Schafer et al. Drug Discovery Today 2008, 13 (21/22), 913-916.*
Horig et al. Journal of Translational Medicine 2004, 2(44).*
Wolff, Burger's Medicinal Chemistry and Drug Discovery, Fifth Edition, vol. I: Principles and Practice, Wiley-Interscience 1995, pp. 974-977.*
Sairam et al "Sildenafil in diabetic peripheral neuropathy", Br. J. Diabetes Vasc. Dis 2002, vol. 2, pp. 304.*
Kristina et al, "Does the cannabinoid dronabinol reduce central pain in multiple sclerosis? Randomized double blind placebo controlled crossover trial", BMJ, Jul. 2004, pp. 1-8.*

(Continued)

*Primary Examiner* — Brandon Fetterolf
*Assistant Examiner* — Jean Cornet
(74) *Attorney, Agent, or Firm* — Rodney L. Sparks

(57) ABSTRACT

Compounds and methods useful for preventing and treating pain, e.g., neuropathic pain, in a subject in need thereof are provided. The compounds can be "S1P modulating" agents that are capable of inducing a detectable change in S1P receptor activity.

18 Claims, 5 Drawing Sheets

OTHER PUBLICATIONS

International Search Report for PCT/US2007/002422.
Bandini, M. et al., *Eur. J. Chem.* 2001, 1937-1942.
Beilstein, Registry No. 6240345.
Bertus, P. et al., *Chem Commun*, 2001, 1792-1793.
Brinkmann, V. et al., *Transplantation* 72, 2001, 764-769.
Brinkmann, V. et al., *J Biol Chem* 277, 2002, 21453-21457.
Burger, A. et al., *Journal of Medicine and Pharmaceutical Chemistry*, vol. 4, No. 3, 1961.
Chiba, K. et al., *J Immunol* 160, 1998, 5037-5044.
Choi, D. et al., *J Med Chem* 39, 1996, 1907-1916.
Clair, T. et al., *Cancer Res* 63, 2003, 5446-5453.
Clemens, J. et al., *Bioorg Med Chem Lett* (2003), 3401-3404.
Clemens, J. et al., *Bioorg. & Med. Chem. Lett.* (2004), 4903-4906.
Clemens, J. et al., *Bioorg. & Med. Chem. Lett.* (2005), 2005, 3568-3572.
Crosignani, S. et al., *Tetrahedron* 54, (1998), 15721-15730.
Davis, M. et al., *The J. of Bio. Chem.*, (2005), 9833-9841.
Dworkin, R. H. et al., *Arch. Neurol.*, 60, 2003, p. 1524-1534.
Forrest, M. et al., *J Pharmacol Exp Ther* 309, 2004, 758-768.
Foss, F. et al., *Bioorganic & Medicinal Chemistry* 15, 2005, 4470-4474.
Foss, F. et al., *Bioorganic & Medicinal Chemistry* 15, 2007, 663-677.
Fujino, M. et al., *J Pharmacol Exp Ther* 305, 2003, 70-77.
Graler, M. H. et al., *FASEB* 18, 2004, 551-553.
Hale, Jeffrey J. et al., *Bioorganic & Medicinal Chemistry Letters* 14, 2004, 3351-3355.
Hale, J. J. et al., 2004 *Bioorg Med Chem Lett* 14, 2004, 3501-3505.
Hale, J. J. et al., (2004) *Bioorg Med Chem Lett* 14, 3495-3499.
Hale, J. J. et al., *J Med Chem*, 2004, 47, 6662-6665.
Hanessian, S. et al., *Bioorganic & Medicinal Chemistry Letters* 17, 2007, 491-494.
Hoshino, Y. et al., (1999) *Transplant Proc* 31, 1224-1226.
Im, D. S. et al., (2000) *J Biol Chem* 275, 14281-14286.
Im, D. S. et al., *Biochemistry* 40, 2001, 14053-14060.
Jones, L. et al., (1997) *J Org Chem* 62, 1388-1410.
Kaiser, C. et al., XP009032189, Nov. 1962, 1243-1265.
Kawasaki, K. et al., *Tetrahedron*, vol. 53, No. 18, 1997, 6337-6350.
Kharel, Y. et al., *J Bio Chem*, vol. 280, No. 44, Nov. 4, 2005, 36865-36872.
Kimura, T. et al., (2003) *Arterioscler Thromb Vasc Biol* 23, 1283-1288.
Kiuchi, M. et al.,(2000) *J Med Chem* 43, 2946-2961.
Kon, J. et al., (1999) *J Biol Chem* 274, 23940-23947.
Kotera et al. Chem. Abst.: Registry Record 19352-04-6.
Lee, M. J. et al., (1998) *Science* 279, 1552-1555.
Lew, M. J. et al., "Analysis of competitive agonist-antagonist interactions by nonlinear regression", (1995) *Trends Pharmacol Sci* 16, 328-337.
Li, Z. et al., *Journal of Medicinal Chemistry*, vol. 48, No. 20, Oct. 6, 2005, 6169-6173.
Maki, T. et al., (2002) *Transplantation* 74, 1684-1686.
Maki, T. et al., (2005) *Transplantation* 79, 1051-1055.
Mandala, S. et al., (2002) *Science* 296, 346-349.
Matloubian, M. et al., (2004) *Nature* 427, 355-360.
Sanchez, T. et al., (2003) *J Biol Chem* 278, 47281-47290.
Sanna, M. G. et al., (2004) *J Biol Chem* 279, 13839-13848.
Sanna, M. G. et al., *Nature Chemical Biology*, vol. 2, Aug. 2006, 434-441.
Suzuki, S. et al., (1996) *Transpl Immunol* 4, 252-255.
Van Brocklyn, J. R. et al., (1999) *J Biol Chem* 274, 4626-4632.
Vogler, R. et al., (2005), No. 20, 2005, 6169-6173.
Xie, J. H. et al., (2003) *J Immunol* 170, 3662-3670.
Yanagawa, Y. et al., (2000) *Int J Immunopharmacol* 22, 597-602.
Yanagawa, Y. et al., (1999) *Transplant Proc* 31, 1227-1229.
Yang, Z., et al., (2003) *Clin Immunol* 107, 30-35.
Zhang, T. et al., (1997) *Cancer Res* 57, 169-175.
Zhang, Y. H. et al., *J Neurophysiol* 96, 2006, 1042-1052.
Zhang, Y. H. et al., *J Physiol* 575.1, 2006, 101-113.

\* cited by examiner

METHOD FOR TREATMENT OF NEUROPATHIC PAIN

CROSS-REFERENCE TO RELATED APPLICATIONS

This application is a continuation of International Application No. PCT/US2007/002422, filed on Jan. 29, 2007, which claims priority under 35 U.S.C. 119 (e) to Provisional Application No. 60/762,589, filed Jan. 27, 2006, the disclosures of which are incorporated by reference in their entirety.

US GOVERNMENT RIGHTS

This invention was made with United States Government support under Grant No. R01 GM067958 awarded by the National Institutes of Health. The United States Government has certain rights in the invention.

FIELD OF THE INVENTION

The present invention relates to sphingosine 1-phosphate analogs, with activity at one or more sphingosine 1-phosphate receptors, which are useful for preventing and treating neuropathic pain.

BACKGROUND

Sphingosine-1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers.

Sphingosine-1-phosphate (S1P) has been demonstrated to induce cellular processes, including those that result in platelet aggregation, cell proliferation, cell morphology, tumor-cell invasion, endothelial cell chemotaxis and endothelial cell in vitro angiogenesis. Therefore, S1P receptors have been targets for therapy of, for example, wound healing and tumor growth inhibition. Sphingosine-1-phosphate is believed to signal cells in part via a set of G protein-coupled receptors named $S1P_1$, $S1P_2$, $S1P_3$, $S1P_4$, and $S1P_5$ (formerly EDG1, EDG5, EDG3, EDG6 and EDG8, respectively). These receptors share 50-55% identical amino acids and cluster with three other receptors ($LPA_1$, $LPA_2$, and $LPA_3$ (formerly EDG2, EDG4 and EDG7, respectively) for the structurally related lysophosphatidic acid (LPA).

S1P receptors have been selected as drug targets because the individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that can initiate or suppress certain cellular responses without affecting other responses. For example, the response specificity of the S1P receptors could allow for an S1P mimetic that initiates platelet aggregation without affecting cell morphology.

Pain can be nociceptive or neuropathic in nature. Neuropathic pain is characterized by its chronic nature, an absence of an obvious direct cause (e.g., tissue damage), hyperalgesia, or allodynia. Hyperalgesia is an exaggerated response to a painful stimulus. Allodynia is the perception of normal stimuli as painful (examples include the touch of clothing, warm or cool air, etc.). Neuropathic pain can be a sequel to nerve damage in an extremity such as an arm, or more often, a leg. Precipitating events can include trauma, e.g., motor vehicle accidents or amputations (e.g., phantom limb pain). Neuropathic pain can occur due to an adverse effect of drug therapies, e.g., vincristine or paclitaxel (Taxol™), or can occur as a component of disease pathologies, such as diabetes type 1 or type 2, shingles, HIV-1 infections, etc. Typically, neuropathic pain does not respond to opiates or non-steroidal anti-inflammatory drugs such as aspirin. Treatment of neuropathic pain is an important unmet medical need and this invention addresses that need.

There is a long felt need in the art for compounds and methods which are useful for preventing and treating pain. The present invention satisfies these needs.

SUMMARY

The present invention provides, in one aspect, compounds and methods useful for preventing and treating pain in a subject in need thereof. The method includes administering to said subject an effective amount of a compound having formula (I) or formula (II):

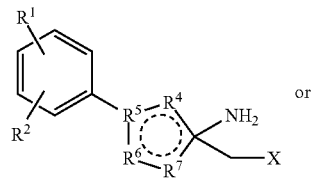

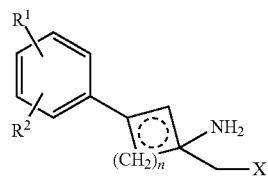

wherein $R^4$ and $R^7$ are independently CH, or $CH_2$, $R^5$ is C, CH, or N, $R^6$ is CH, $CH_2$, O, S or $NR^3$, $R^3$ is hydrogen, or an alkyl group.

X is hydroxyl (—OH), phosphate (—$OPO_3H_2$), phosphonate (—$CH_2PO_3H_2$), or alpha-substituted phosphonate, $R^1$ is hydrogen, halo, tri-fluoromethyl, ($C_1$-$C_{10}$)-alkyl, ($C_1$-$C_{10}$) alkyl substituted with halo, hydroxy, alkoxy, or cyano, $R^2$ is ($C_1$-$C_{20}$)alkyl, cycloalkyl substituted alkyl, ($C_2$-$C_{20}$)alkenyl, ($C_2$-$C_{20}$)alkynyl, aryl, alkyl substituted aryl, arylalkyl, or aryl substituted arylalkyl, wherein one or more of the carbon atoms in the $R^2$ groups can be independently replaced with non-peroxide oxygen, sulfur or $NR^8$, wherein $R^8$ is hydrogen, or an ($C_1$-$C_{10}$) alkyl group, wherein the alkyl, alkenyl, and alkynyl groups in $R^2$ are optionally substituted with oxo, n is 0, 1, 2 or 3, and

represents 1, 2, or 3, optional double bonds, or a pharmaceutically acceptable salt or ester thereof.

In another aspect, the present invention provides for the use of a compound of formula (I), formula (II), or a pharmaceutically acceptable salt thereof to prepare a medicament for preventing and treating pain in a mammal (e.g., a human).

DETAILED DESCRIPTION

Figure 1:
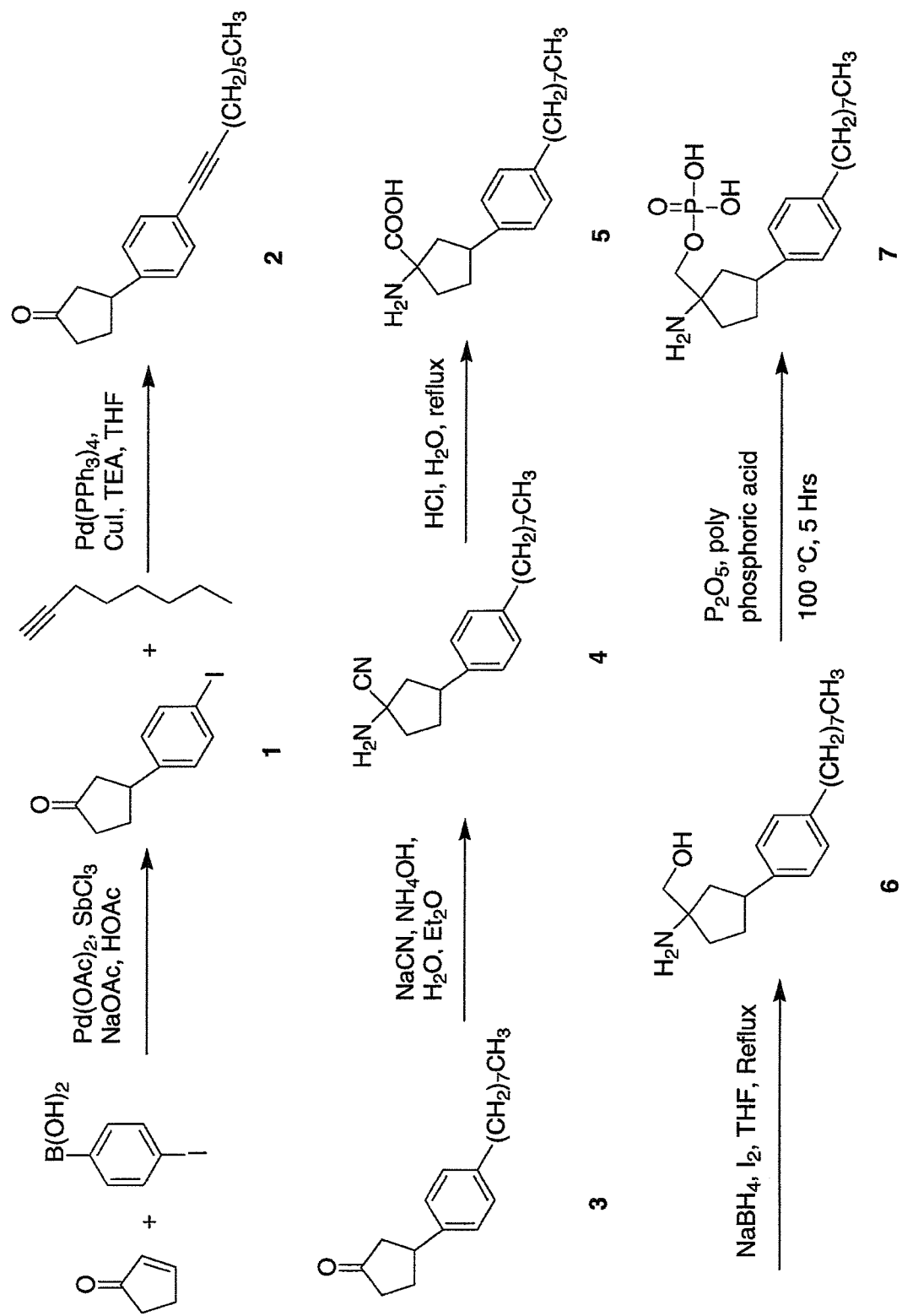
FIG. 1 is an illustration of a synthetic route to prepare compounds used in the disclosed method.

The following abbreviations are used herein: S1P, sphingosine-1-phosphate; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; and RT-PCR, reverse transcriptase polymerase chain reaction Unless defined otherwise, all technical and scientific terms used herein have the same meaning as commonly understood by one of ordinary skill in the art to which this invention belongs. Although any methods and materials similar or equivalent to those described herein can be used in the practice or testing, the preferred methods and materials are described herein. The following terms have the meaning associated with it in this section.

The articles "a" and "an" are used herein to refer to one or to more than one (e.g., to at least one) of the grammatical object of the article. By way of example, "an element" means one element or more than one element.

The term "affected cell" refers to a cell of a subject afflicted with a disease or disorder, which affected cell has an altered phenotype relative to a subject not afflicted with a disease or disorder. Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

The terms "cell," "cell line," and "cell culture" may be used interchangeably. A "test" cell, tissue, sample, or subject is one being examined or treated. A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "pathoindicative" cell, tissue, or sample is one which, when present, is an indication that the animal in which the cell, tissue, or sample is located (or from which the tissue was obtained) is afflicted with a disease or disorder. For example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The word "detect" and its grammatical variants refer to measurement of the species without quantification. The terms "detect" and "identify" are used interchangeably herein. The words "determine" or "measure" and their grammatical variants refer to measurement of the species with quantification. The terms "determine" or "measure" are used interchangeably herein.

A "detectable marker" or a "reporter molecule" is an atom or a molecule that permits the specific detection of a compound comprising the marker in the presence of similar compounds without a marker. Examples of detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "effective amount" means an amount sufficient to produce a selected effect. For example, an effective amount of an S1P receptor antagonist is an amount that decreases the cell signaling activity of the S1P receptor.

A "functional" molecule is a molecule in a form in which it exhibits a property by which it is characterized. For example, a functional enzyme is one which exhibits the catalytic activity by which the enzyme is characterized.

The term "inhibit" refers to the ability of a compound to reduce or impede a described function. Preferably, inhibition is by at least 10%, more preferably by at least 25%, even more preferably by at least 50%, and most preferably, the function is inhibited by at least 75%.

The term "instructional material" includes a publication, a recording, a diagram, or any other medium of expression, which can be used to communicate the usefulness, in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains an active compound or be shipped together with a container which contains an active compound. Alternatively, the instructional material may be shipped separately from the container with the intention that the instructional material and an active compound be used cooperatively by the recipient.

The term, "parenteral" means not through the alimentary canal but by some other route such as subcutaneous, intramuscular, intraspinal, or intravenous.

The term "pharmaceutically acceptable carrier" includes any of the standard pharmaceutical carriers, e.g., a phosphate buffered saline solution, water and emulsions such as an oil/water or water/oil emulsion, and various types of wetting agents.

The term "purified" and similar terms relate to the isolation of a molecule or compound in a form that is substantially free (at least 60% free, preferably 75% free, and most preferably 90% free) from other components normally associated with the molecule or compound in a native environment.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject that contains cells, tissues, or a fluid of interest. A sample can also be obtained from a cell or tissue culture.

The terms "standard" or "control" are used interchangeably herein and refer to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "treating" includes prophylaxis of the specific disorder or condition, or alleviation of the symptoms associated with a specific disorder or condition and/or preventing or eliminating said symptoms.

As used herein, the term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

As used herein, the term "pharmaceutically-acceptable salt" refers to salts which retain the biological effectiveness and properties of compounds for practicing the disclosed method and which are not biologically or otherwise undesirable. In many cases, the compounds for practicing the disclosed method are capable of forming acid and/or base salts by virtue of the presence of amino and/or carboxyl groups or groups similar thereto.

The general chemical terms used in the description of the compounds for practicing the disclosed method have their usual meanings. For example, the term "alkyl" by itself or as part of another substituent means a straight or branched aliphatic chain having the stated number of carbon atoms.

The term "halo" or "halogen" includes bromo, chloro, fluoro, and iodo.

The term "haloalkyl" refers to an alkyl radical bearing at least one halogen substituent, for example, chloromethyl, fluoroethyl or trifluoromethyl and the like.

The term "alkyl or $C_1$-$C_{10}$ alkyl" represents a branched or linear alkyl group having from one to six carbon atoms. Typically $C_1$-$C_{10}$ alkyl groups include, but are not limited to, methyl, ethyl, n-propyl, iso-propyl, butyl, iso-butyl, sec-butyl, t-butyl, pentyl, hexyl, heptyl, octyl, and the like. The term "lower alkyl" refers to branched or straight chain alkyl groups comprising one to about six carbon atoms, including methyl, ethyl, propyl, isopropyl, n-butyl, t-butyl, neopentyl and the like.

The term "alkenyl or $C_2$-$C_{10}$ alkenyl" represents an olefinically unsaturated branched or linear group having from 2 to 10 carbon atoms and at least one double bond. Examples of such groups include, but are not limited to, 1-propenyl, 2-propenyl, 1,3-butadienyl, 1-butenyl, hexenyl, pentenyl, and the like.

The term "alkynyl or $C_2$-$C_{10}$ alkynyl," refers to an unsaturated branched or linear group having from 2 to 10 carbon atoms and at least one triple bond. Examples of such groups include, but are not limited to, 1-propynyl, 2-propynyl, 1-butynyl, 2-butynyl, 1-pentynyl, and the like.

The term "$C_3$-$C_8$ cycloalkyl," represents cyclopropyl, cyclobutyl, cyclopentyl, cyclohexyl, cycloheptyl, cyclooctyl and the like.

The term "optionally substituted" refers to substitution with from zero to four substituents, wherein the substituents are each independently selected. Each of the independently selected substituents may be the same or different than other substituents.

As used herein the term "aryl" refers to a mono or bicyclic $C_5$-$C_{10}$ carbocyclic ring system having one or two aromatic rings including, but not limited to, phenyl, benzyl, naphthyl, tetrahydronaphthyl, indanyl, indenyl, and the like. The term "optionally substituted aryl" includes aryl compounds having from zero to four substituents, and a "substituted aryl" includes aryl compounds having one to four substituents, wherein the substituents include groups such as, for example, alkyl, halo or amino substituents.

The term "arylalkyl" refers to any aryl group which is attached to the parent moiety via the alkyl group, e.g., aryl ($C_1$-$C_8$ alkyl). Thus, the term ($C_5$-$C_6$ aryl)($C_5$-$C_8$ alkyl) refers to a five or six membered aromatic ring that is attached to the parent moiety via the $C_5$-$C_8$ alkyl group.

The term "heterocyclic group" refers to an optionally substituted mono- or bicyclic carbocyclic ring system containing from one to three heteroatoms wherein the heteroatoms are oxygen, sulfur, or nitrogen.

As used herein the term "heteroaryl" refers to an optionally substituted mono- or bicyclic carbocyclic ring system having one or two aromatic rings containing from one to three heteroatoms wherein the heteroatoms are oxygen, sulfur, or nitrogen. Examples of heteroaryl rings include, but are not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "$EC_{50}$ of an agent" refers to that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% is set at the amount of activity in the assay in the absence of added ligand/agonist.

The terms "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., hydrogen, $NH_4$, Na, and the like if such counterions are present.

The compounds for practicing the disclosed method may exist in tautomeric forms and include both mixtures and separate individual tautomers. For example, the following structure:

is understood to represent a mixture of the structures:

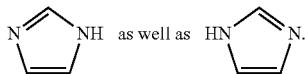

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

As used herein, an "S1P modulating agent" refers to a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," as used herein, refers to all of the S1P receptor subtypes (for example, the S1P receptors $S1P_1$, $S1P_2$, $S1P_3$, $S1P_4$, and $S1P_5$), unless the specific subtype is indicated.

The S1P analogs for practicing the disclosed method can contain one or more asymmetric centers in the molecule. A structure that does not designate the stereochemistry is to be understood as embracing all the various optical isomers, as well as racemic mixtures thereof.

The disclosed method includes the use of sphingosine 1-phosphate (S1P) analogs that have activity as receptor agonists at one or more S1P receptors, specifically the $S1P_1$, $S1P_4$ and $S1P_5$ receptor types. The disclosed method also includes compounds that have a phosphate moiety as well as compounds with hydrolysis-resistant phosphate surrogates such as phosphonates, alpha-substituted phosphonates particularly where the alpha substitution is a halogen and phosphothionates.

In one embodiment, the S1P receptor agonists have the general structure of Formula (IIA):

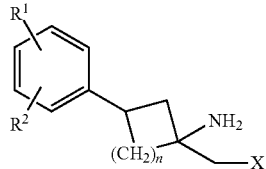

IIA wherein n is 0, 1, 2 or 3, X is hydroxyl (—OH), phosphate (—$OPO_3H_2$), phosphonate (—$CH_2PO_3H_2$), or alpha-substituted phosphonate (including: —$CHFPO_3H_2$, —$CF_2PO_3H_2$, —$CHOHPO_3H_2$, —C=$OPO_3H_2$), wherein $R^1$ is hydrogen, halogens (wherein F or Cl are the preferred halogens), ($C_1$-$C_6$) alkyl, such as, methyl, ethyl, and propyl, or halo-, hydroxy-, alkoxy-, cyano-, or substituted ($C_1$-$C_6$) alkyl, such as, tri-fluoromethyl. The $R^2$ group is alkyl, alkenyl, alkynyl, alkyl substituted aryl, alkyl substituted cycloalkyl, arylalkyl or arylalkyl substituted aryl. In $R^2$ the chain lengths of 5-8 carbon atoms are preferred, or a pharmaceutically acceptable salt thereof.

In a specific embodiment, of the compounds having formula (IIA), $R^1$ is hydrogen, halo (e.g., F or Cl), methyl, tri-fluoromethyl, ethyl, propyl, other lower alkyl ($C_1$-$C_6$) or halo-, hydroxy-, alkoxy-, cyano-substituted lower alkyl group, and $R_2$ is alkyl, alkenyl, alkynyl, alkyl (optionally substituted aryl), alkyl (optionally substituted cycloalkyl), arylalkyl, or arylalkyl (optionally substituted aryl) with chain lengths of 5-8 carbon atoms preferred.

The invention provides a method for treating neuropathic pain including administering to a subject in need thereof of a therapeutically acceptable amount of a compound of formula (I) or formula (II), or a pharmaceutical composition comprising a therapeutically effective amount of a compound of formula (I) or formula (II), and a pharmaceutically-acceptable carrier.

The disclosed method also includes the use of pharmaceutical compositions including a compound of formula (I) or formula (II), and a pharmaceutically-acceptable carrier. The compounds of formula (I) or formula (II) can be formulated as pharmaceutical compositions using standard pharmaceutically acceptable carriers, fillers, solubilizing agents and stabilizers known to those skilled in the art. For example, a pharmaceutical composition comprising a compound of formula (I) or formula (II), or analog, derivative, or modification thereof, as described herein, is used to administer the compound to a subject.

A specific value for a lower alkyl group is ethyl or propyl.
A specific value for halo is fluorine or chlorine.
A specific value for X is hydroxy or $OPO_3H_2$.
A specific value for the alpha-substituted phosphonate group is $CHFPO_3H_2$, $CF_2PO_3H_2$, $CHOHPO_3H_2$, —C=$OPO_3H_2$) or thiophosphate ($OPO_2SH_2$).
A specific value for $R^1$ is hydrogen.
A specific value for $R^2$ is $C_5$-$C_8$alkyl.
A more specific value for $R^2$ is heptyl, octyl, nonyl, —O-heptyl, —C(=O)heptyl, or $CH_3$—$CH_2$—O—$CH_2$—$CH_2$—O—$CH_2$—$CH_2$—O—.
A more specific value for $R^2$ is octyl, or —O-heptyl.
A more specific value for $R^2$ is octyl.
A specific value for n is 1 or 2.

Specific cycloalkyl groups having a double bond include:

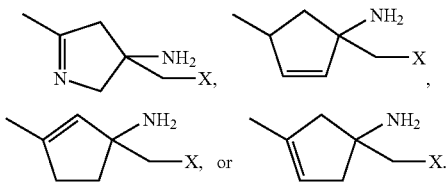

A compound for practicing the disclosed method has an $R^2$ group placed para to the cycloalkyl ring.

A specific compound for practicing the disclosed method has the $R^1$ group placed ortho or meta to $R^2$.

A specific compound for practicing the disclosed method has the $R^2$ group placed para to the benzylic cycloalkyl group (e.g., 1,4).

Non-limiting examples of esters of the disclosed compounds include compounds where the X group is,

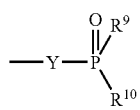

wherein Y is O, $CH_2$, CHOH, CHF, $CF_2$, or

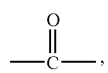

and $R^9$ and $R^{10}$ are independently alkoxy, alkenyloxy, alkynyloxy, aryloxy,

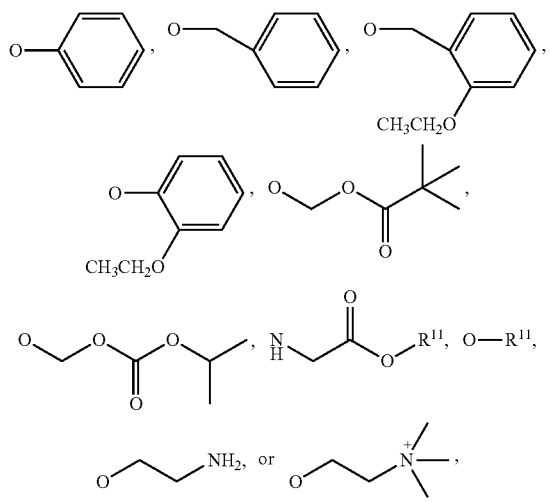

wherein $R^{11}$ is $C_1$-$C_4$ alkyl, $C_2$-$C_4$ alkenyl, $C_2$-$C_4$ alkynyl, or optionally substituted aryl. Particularly preferred $R^9$ and $R^{10}$ groups are alkoxy,

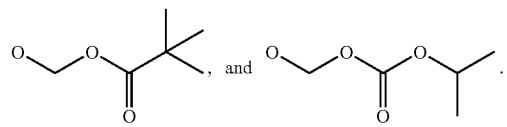

A specific compound of formula (II) is VPC01091, where X is OH, $R^1$ is hydrogen, $R^2$ is octane ($C_8H_{17}$), n is 2, and the $R^2$ group is in the para-position on the phenyl ring. The formula is:

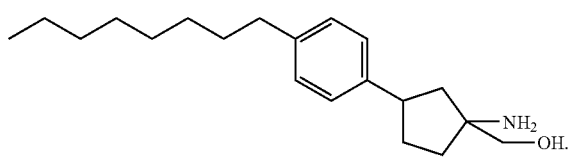

VPC01091

VPC01091 has two chiral centers (the quaternary carbon and benzylic carbon that is part of the cyclopentyl ring) and thus four isomers (diastereomers) are conceivable. VPC01091 is a mixture of these four isomers but the relative amount of each isomer is not known, but available evidence indicates that the four isomers are present in about equal amounts. The individual isomers, A-D, have the formulas:

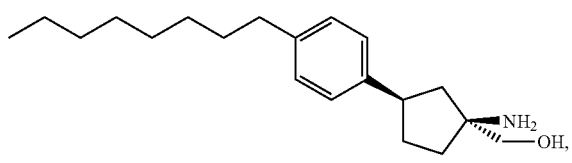

VPC01091-A

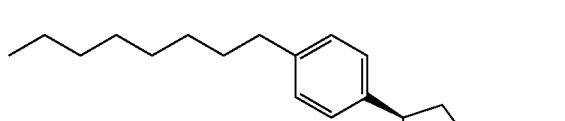

VPC01091-B

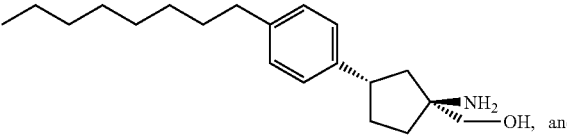

VPC01091-C

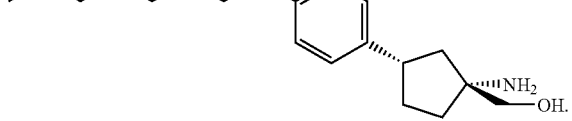

VPC01091-D

These compounds can be prepared as a mixture and separated by chromatography. Exemplary conditions for separation are as follows: Column: Chiralpak AD 4.6 mm ID×250 mm, Mobile Phase: Hex/EtOH/MeOH/DEA=95/2.5/2.5/0.03, Flow Rate: 1 mL/min, Detector: UV 220 nm, Column Temp: 40° C., or Column Temp: 25° C. The order of isomer elution was D, C, B, and A. After separation, it was found that two isomers, B and D, were not phosphorylated by the SPHK2 enzyme in vitro. However, when phosphorylated prior to testing the phosphorylated compounds were found to be active agonists of the S1P receptors.

Another specific compound of formula (II) is VPC01211 where X is $OPO_3H_2$, $R^1$ is hydrogen, $R^2$ is octane ($C_8H_{17}$), n is 2, and the $R^2$ group is in the para-position on the phenyl ring. The formula is:

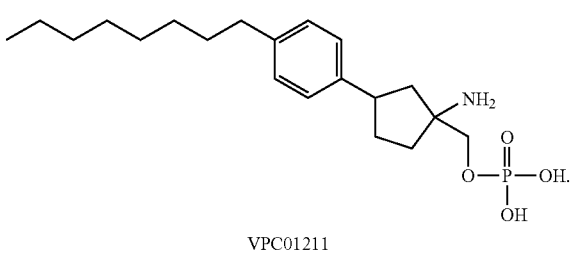

VPC01211

Another specific compound of formula (II) is VPC02162, where X is OH, $R^1$ is hydrogen, $R^2$ is octane ($C_8H_{17}$), n is 2, and the $R^2$ group is in the meta-position on the phenyl ring. The formula is:

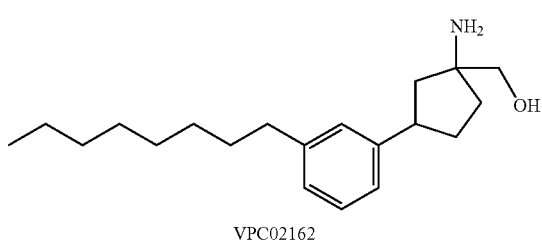

VPC02162

Another specific compound of formula (II) is VPC02164 where X is $OPO_3H_2$, $R^1$ is hydrogen, $R^2$ is octane ($C_8H_{17}$), n is 2, and the $R^2$ group is in the meta-position on the phenyl ring. The formula is:

VPC02164

Additional examples of disclosed compounds that include heteroatoms (e.g., N, S, O) and/or double bonds in the cycloalkyl ring include the structures below:

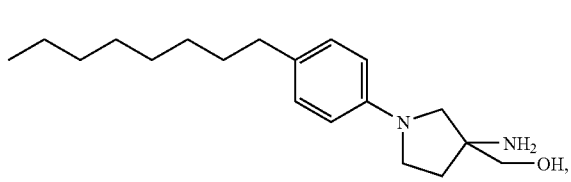

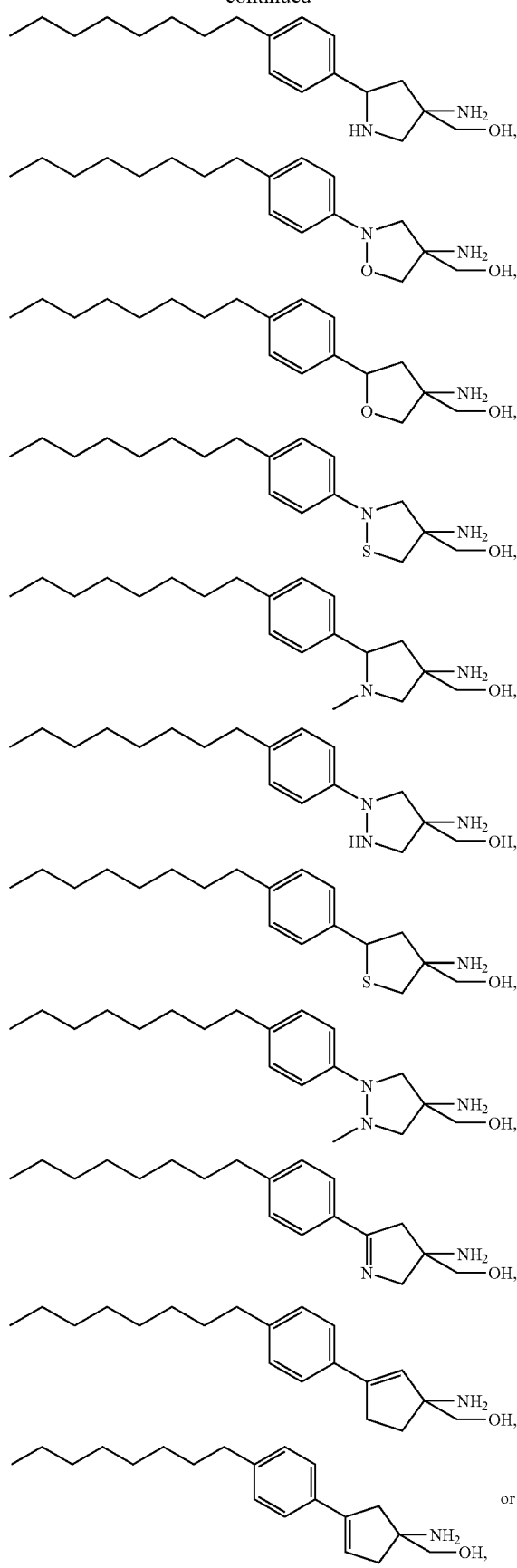

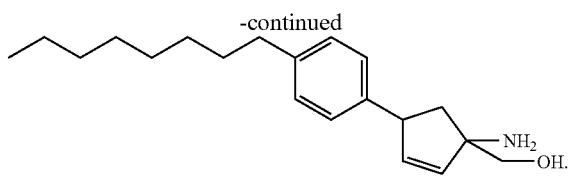

A synthetic route to prepare compound for practicing the disclosed method, VPC01091 (6) and VPC01211 (7), is provided in the scheme in FIG. 1. Additional compounds of formula (I) or formula (II) can be prepared by a person skilled in the art using known modifications to procedures from the schemes and detailed descriptions in the specific examples herein.

Additional compounds of formula (I) or formula (II) having the general formula (III) are illustrated below. The specific variables are recited in Table 1:

TABLE 1

(III)

| Compound | R | n | X |
|---|---|---|---|
| VPC02004 | $C_7H_{15}$ | 2 | OH |
| VPC02007 | $C_7H_{15}$ | 2 | $OPO_3H_2$ |
| VPC01091 | $C_8H_{17}$ | 2 | OH |
| VPC01211 | $C_8H_{17}$ | 2 | $OPO_3H_2$ |
| VPC02031 | $C_9H_{19}$ | 2 | OH |
| VPC02033 | $C_9H_{19}$ | 2 | $OPO_3H_2$ |
| VPC01289 | $C_{10}H_{21}$ | 2 | OH |
| VPC01292 | $C_{10}H_{21}$ | 2 | $OPO_3H_2$ |
| VPC01220 | $C_8H_{17}$ | 1 | OH |
| VPC01222 | $C_8H_{17}$ | 1 | $OPO_3H_2$ |
| VPC01213 | $C_8H_{17}$ | 3 | OH |
| VPC01214 | $C_8H_{17}$ | 3 | $OPO_3H_2$ |

The present invention also provides a method for the use of esters of the compounds of formula (I) or formula (II), e.g., phosphate esters or phosphonate esters as described herein. In addition, the disclosed method includes pharmaceutically acceptable salts of the compounds of formula (I) or formula (II). The disclosed method provides all possible isomers of the structures described by formula (I) or formula (II), noting that when n is one (cyclobutane) the compound is symmetric and lacks chiral centers, but cis and trans forms exist.

Pharmaceutical compositions comprising one or more disclosed compounds can be administered to a subject in need thereof by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. The oral route is typically employed for most conditions requiring the disclosed compounds. Preference is given to intravenous injection or infusion for the acute treatments. For maintenance regimens, the oral or parenteral, e.g. intramuscular or subcutaneous, route is preferred.

One of ordinary skill in the art would appreciate that the disclosed compounds can be administered at varying doses and at varying times, depending on such conditions as the health, age, weight, and sex of the subject. One of ordinary skill in the art would also appreciate that the disclosed compounds can be administered to a subject via different routes.

In accordance with one aspect, the method provides administration of a composition that includes a disclosed compound, or an analog, derivative, or modification thereof, and albumin, e.g., the composition comprises at least one disclosed compound, a pharmaceutically acceptable carrier and 0.1-1.0% albumin. Albumin can function as a buffer to improve the solubility of the compounds. In one aspect, albumin is not added.

In one aspect, the pharmaceutical compositions useful for practicing the disclosed method may be administered to deliver a dose of between 1 ng/kg/day and 100 mg/kg/day. In another embodiment, the pharmaceutical compositions useful for practicing the disclosed method may be administered to deliver a dose of between 1 ng/kg/day and 100 g/kg/day.

Pharmaceutically acceptable carriers which are useful include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Modification of pharmaceutical compositions for administration to humans in order to prepare the compositions for administration to various animals is well understood, and the ordinarily skilled veterinary pharmacologist can design and perform such modification with merely ordinary, if any, experimentation. Subjects to which administration of the pharmaceutical compositions of the disclosed method is contemplated include, but are not limited to, humans and other primates, and mammals, including commercially relevant mammals such as cattle, pigs, horses, sheep, cats, and dogs.

A pharmaceutical composition may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in the pharmaceutical compositions will vary, depending upon the identity, size, and condition of the subject treated and further depending upon the route by which the composition is to be administered. By way of example, the composition may comprise between 0.1% and 100% (w/w) active ingredient.

In addition to the active ingredient, pharmaceutical compositions may further comprise one or more additional pharmaceutically active agents. Particularly contemplated additional agents include anti-emetics and scavengers such as cyanide and cyanate scavengers.

Controlled- or sustained-release formulations of a pharmaceutical composition may be made using conventional technology.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Controlled-release formulations known to those of ordinary skill in the art, including those described herein, can be readily selected for use with the pharmaceutical compositions. Thus, single unit dosage forms for oral administration, such as tablets, capsules, gelcaps, and caplets that are adapted for controlled-release are encompassed by the disclosed method.

Most controlled-release formulations are designed to initially release an amount of drug that promptly produces the desired therapeutic effect, and gradually and continually release other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds.

Powdered and granular formulations of a pharmaceutical preparation may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

As used herein, an "oily" liquid is one which comprises a carbon-containing liquid molecule and which exhibits a less polar character than water.

A formulation of a pharmaceutical composition for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

The disclosed method includes a kit comprising a compound or composition useful for preventing or treating pain in a subject and an instructional material which describes administering the compound or a composition comprising the compound to a cell or an animal. This should be construed to include other embodiments of kits that are known to those skilled in the art, such as a kit comprising a (preferably sterile) solvent for dissolving or suspending the disclosed composition prior to administering the compound to a cell or an animal. Preferably the animal is a human.

It will be appreciated by those skilled in the art that the disclosed compounds having a chiral center may exist in and be isolated in optically active and racemic forms. Some compounds may exhibit polymorphism. It is to be understood that any racemic, optically-active, polymorphic, or stereoisomeric form, or mixtures thereof, of a disclosed compound, which possess the useful properties described herein is included. It is known in the art how to prepare optically active forms (for example, resolution of the racemic form by recrystallization techniques, synthesis from optically-active starting materials, by chiral synthesis, or chromatographic separation using a chiral stationary phase) and how to determine S1P agonist activity using the standard tests described herein, or using other similar tests which are well known in the art.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Non-limiting examples of amines include isopropyl amine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in to practice the disclosed method, for example, carboxylic acid amides, including carboxamides, lower alkyl carboxamides, dialkyl carboxamides, and the like.

Salts may be obtained using standard procedures well known in the art. For example reaction of a sufficiently basic compound such as an amine with an acid can afford a physiologically acceptable anion. Alkali metal (for example, sodium, potassium or lithium) or alkaline earth metal (for example calcium) salts of organic (e.g., carboxylic) acids can also be made.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

Example 1

(1-amino-3-(4-octylphenyl)cyclopentyl)methanol (6)

A.: 3-(4-iodophenyl)cyclopentanone (1) 0.23 g palladium (II) acetate (0.1 eq) and 0.23 g antimony(III) chloride (0.1 eq) were added to 80 mL acetic acid solution of 2-cyclopenten-1-one 0.82 g (10 mmol), 4-iodophenylboronic acid 2.48 g (10 mmol) and sodium acetate 1.6 g (20 mmol) under $N_2$ atmosphere. After being stirred for 24 hours at 25° C., the black precipitation was filtered off and the filtrate was diluted with 250 mL of brine, and then extracted twice with 50 mL methylene chloride. The organic extract was stirred with saturated $NaHCO_3$ solution for 30 minutes, then washed with brine and dried over $MgSO_4$. Removal of solvent resulted in a yellow oil, further purification by flash column (chloroform) gave 1.92 g (67%) product as a white solid. *J. Org. Chem.*, 1995, 60, 883-888. $^1H$ NMR ($CDCl_3$) δ 7.63 (d, 2H, ArH), 7.00 (d, 2H, ArH), 3.35 (m, 1H, ArCHCC), 2.7-1.8 (m, 6H, cyclopentyl); 13C NMR ($CDCl_3$) δ 218, 143, 138, 129, 95, 46, 42, 39, 31.

B.: 3-(4-(oct-1-ynyl)phenyl)cyclopentanone (2) 1.1 g (10 mmol) of 1-octyne was added to a flame dried 25 mL flask charged with 10 mL THF solution of 1.43 g (5 mmol) of 1. After degassing for 30 minutes, 2 mL triethylamine, 5 mg of CuI and 10 mg of $Pd(PPh_3)_4$ were added under $N_2$ protection. The reaction was complete in 6 hrs, after removal of solvent and volatile reagent, the mixture was column chromatographed with chloroform to provide 1.34 g (99%) yellow oil. $^1H$ NMR ($CDCl_3$) δ 7.35 (d, 2H, ArH), 7.15 (d, 2H, ArH), 3.37 (m, 1H, ArCHCC), 2.7-2.2 (m, 6H, cyclo-pentyl), 1.95 (m, 2H, $CCCH_2CH_2$), 1.6-1.2 (m, 8H, $CH_2$), 0.89 (t, J=6 Hz, 2H, $CH_3$); $^{13}C$ NMR ($CDCl_3$) δ 220, 143, 132, 127, 122, 91, 80, 46, 42, 39, 32, 31, 29, 29, 23, 20, 14.

C.: 3-(4-octylphenyl)cyclopentanone (3). Several drops of formic acid and catalytic amount 5% Pd/C was added to a 25 mL flask charged with 10 mL methanol and 1.34 g (5 mmol) of 2. The reaction vessel was flushed with $H_2$, 3 times, and then mounted with a $H_2$ balloon. After two days of hydrogenolysis, the solute was filtered through a pad of silica, and concentrated to provide a yellow oil. 1.32 g (98%) product was collected. $^1H$ NMR ($CDCl_3$) δ 7.18 (s, 4H, ArH), 3.38 (m, 1H, ArCHCC), 2.60 (t, 2H, $CCCH_2CH_2$), 2.45-1.91 (m, 6H, cyclo-pentyl), 1.64-1.15 (m, 12H, $CH_2$), 0.90 (t, 3H, $CH_3$); $^{13}C$ NMR ($CDCl_3$) δ 220, 142, 140, 129, 127, 46, 42, 39, 36, 32, 32, 32, 30, 30, 29, 23, 14.

D.: 1-amino-3-(4-octylphenyl)cyclopentanecarbonitrile (4) 3.20 g (11.8 mmol) of 3, sodium cyanide 1.15 g (23.5 mmol) and ammonium chloride 1.25 g (23.5 mmol) were added to 20 mL of ammonium hydroxide. The mixture was extracted twice with 10 mL of methylene chloride after vigorously stirring overnight. The organic extraction was dried and concentrated to provide a yellow oil 3.30 g. The crude product is used for next step without further purification. *J. Med. Chem.*, 1986, 29, 1988-1995.

E.: 1-amino-3-(4-octylphenyl)cyclopentanecarboxylic acid (5). 3.3 g (11.2 mmol) of 4 and 50 mL concentrated hydrochloric acid was heated to 70° C. and stirred overnight. The resulting clear aqueous solution was evaporated to dryness. 10 mL water was added and dried again. This process was repeated several times. The crude product was washed with water and acetone to provide a white fine powder. Yield was 1.7 g (45%). $^1H$ NMR ($d^6$-DMSO) δ 7.25-7.06 (m, 4H, ArH), 3.21 (m, 1H, ArCHCC), 2.38-1.62 (m, 6H, cyclo-pentyl), 1.49-1.20 (m, 14H, $CH_2$), 0.81 (t, J=6 Hz, 3H, $CH_3$); $^{13}C$ NMR ($d^6$-DMSO) δ 175, 141, 140, 64, 51, 46, 45, 44, 36, 35, 35, 34, 32, 32, 29, 29, 23, 15.

F.: (1-amino-3-(4-octylphenyl)cyclopentyl)methanol (6). 63.4 mg (0.2 mmol) of 5 and 27 mg (0.6 mmol) sodium borohydride were dissolved in 3 mL of THF. After the solution was cooled to 0° C., 51 mg (0.2 mmol) $I_2$ was dissolved in 1 mL THF and added dropwise. Then the vessel was fitted with a condenser and the reaction mixture was refluxed under $N_2$ for 5 hrs. Excess $NaBH_4$ was quenched with methanol. After removal of solvent, 2 mL water and 5 mL methylene chloride was added, the mixture was stirred for about 1 hr until the organic layer became clear. The organic phase was collected and aqueous phase was further extracted twice with methylene chloride. The combined organic extraction was dried and concentrated to provide 43 mg (71%) of the crude product. Further purification on TLC with methanol/chloroform (5:95) provided 13 mg of clear oil. *J. Org. Chem.*, 1993, 58, 3568-3571. $^1H$ NMR ($CD_3OD$) δ 7.11 (m, 4H, ArH), 3.80 (t, J=7.5 Hz, 1H, c-pentyl-$CH_2O$), 3.67 (t, J=7.5 Hz, 1H, c-pentyl-$CH_2O$), 3.01 (m, 1H, ArCHCC), 2.55 (t, J=7.5 Hz, 2H, $ArCH_2$), 2.29-1.69 (m, 6H, cyclo-pentyl), 1.57 (m, 2H, $ArCH_2CH_2$), 1.38-1.28 (m, 10H, $CH_2$), 0.89 (t, J=7.5 Hz, 3H, $CH_3$); $^{13}C$ NMR ($CD_3COCD_3$) δ 141, 128, 127, 96, 45, 44, 43, 35, 35, 33, 33, 32, 32, 29, 29, 29, 23, 13.

Example 2

(1-amino-3-(4-octylphenyl)cyclopentyl)methyl dihydrogen phosphate (7)

1 mL of 85% $H_3PO_4$ was slowly added (by drops) into 0.5 g of $P_2O_5$, the acid-anhydride mixture was then heated at 100° C. for 1 hour under nitrogen protection. Another 0.5 g of $P_2O_5$ and 30 mg of alcohol 6 were added to the poly phosphoric acid and heated for 5 hours at 100° C. After cooling down to room temperature, 10 mL cold water (0° C.) was added to reaction mixture. The product precipitated out as white solid, was collected and washed with water. 31 mg (82%) of green colored product was collected after vacuum drying. MS only two peaks: M+1=384.4 with 304.4 (hydrolyzed back to 6).

Example 3

Separation of Isomers of VPC01091

The mixture of isomers of compound VPC01091 is preformed using a Chiralpak AD-H 4.6 mm ID×250 mm column, at 45° C., solvent flow rate: 0.8 mL/min (isocratic), solvent: 95% heptane: 2.5% ethanol: 2.5% methanol (0.2% diethylamine added as modifier to 95:2.5:2.5 mixture). The run time was 40 min, $UV_1$, wavelength monitored: 254 nm. The order of isomer elution was D, C, B, and A.

Example 4

Pain Assay

Test compound, VPC01091 (Drug T, mixture of all isomers), was dissolved in 2% hydroxypropyl beta-cyclodextrin in water and administered to the test group of laboratory rats. The vehicle (Drug V: 2% hydroxypropyl beta-cyclodextrin in water) was administered to the control group of laboratory rats. Each group included 11 animals.

The identities of 'Drug T' and 'Drug V' were maintained in secret to prevent bias. The test solutions (test compound or vehicle) were intraperitoneally (IP) administered once (day 0), the dose was 10 mg/kg body weight. On day 0, each of the 22 animals was anesthetized, the sciatic nerve bundle on the right side exposed surgically, and crushed mechanically. This is known as the 'trauma' model of neuropathic pain. The animals were tested each day for the time required to lift either paw after illumination with small heat lamp. Normal PWL (paw withdrawal latency) time in an adult rat is 10-11 seconds, an untreated rat with a crushed sciatic nerve exhibits thermal hyperalgesia having a PWL time decreases to about 6 seconds.

Figure 2:
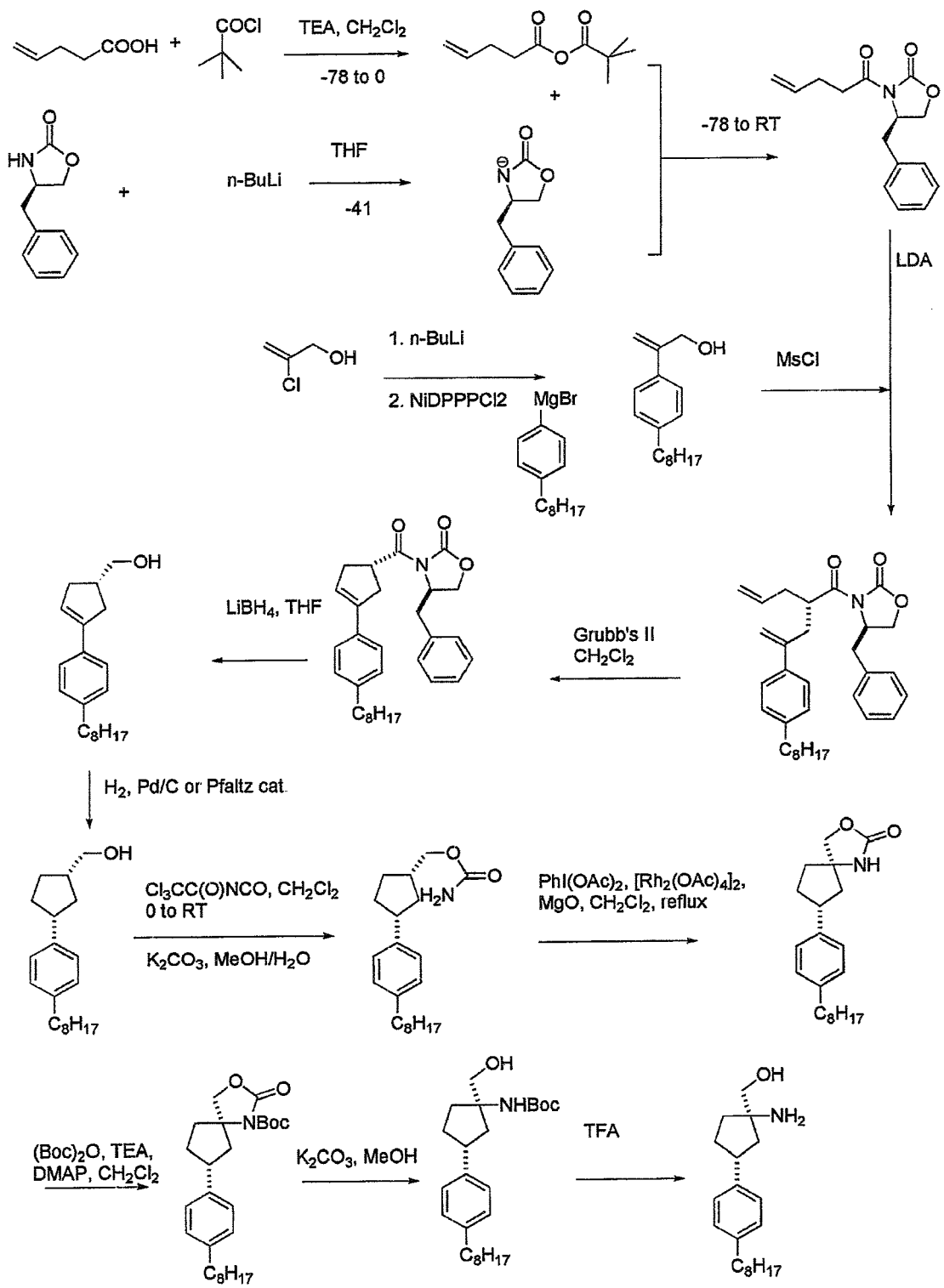
FIG. 2 is an illustration of a synthetic route to prepare the compound VPC01091-C.
Figure 3:
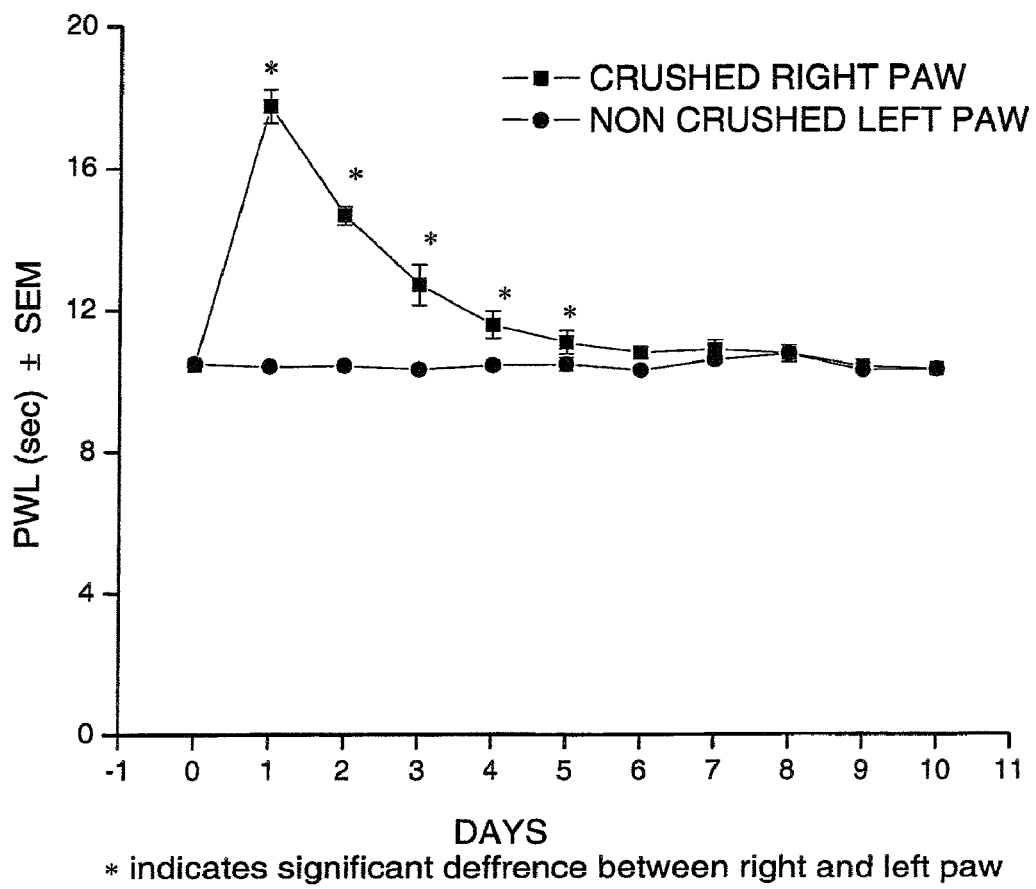
FIG. 3 is a graphical representation of the results from administration of a compound of formula VPC01091.
Figure 4:
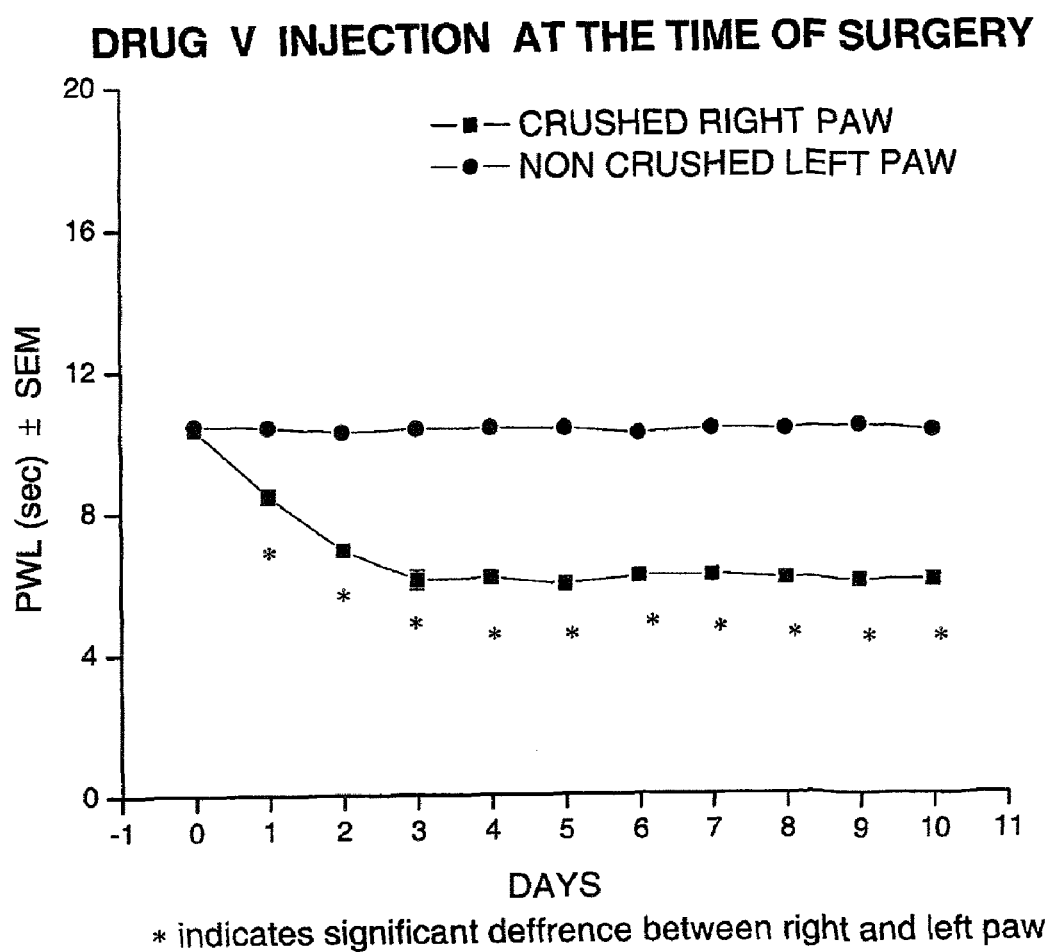
FIG. 4 is a graphical representation of the results from administration of a vehicle control.

Treatment of the animals with VPC01091 (Drug T) prevented the development of thermal hyperalgesia in the affected (crushed nerve) paw, and exhibited an analgesic effect, due to PWL time increases after injury, only on the affected side. The results are illustrated in FIGS. 2 and 3.

Other, non-S1P receptor active, compounds that prevent thermal (or mechanical) allodynia from developing in such models are known. Likewise, drugs that cause general analgesia (e.g., morphine) are known.

Example 5

Analgesic Effects of VPC01091-D

Figure 5:
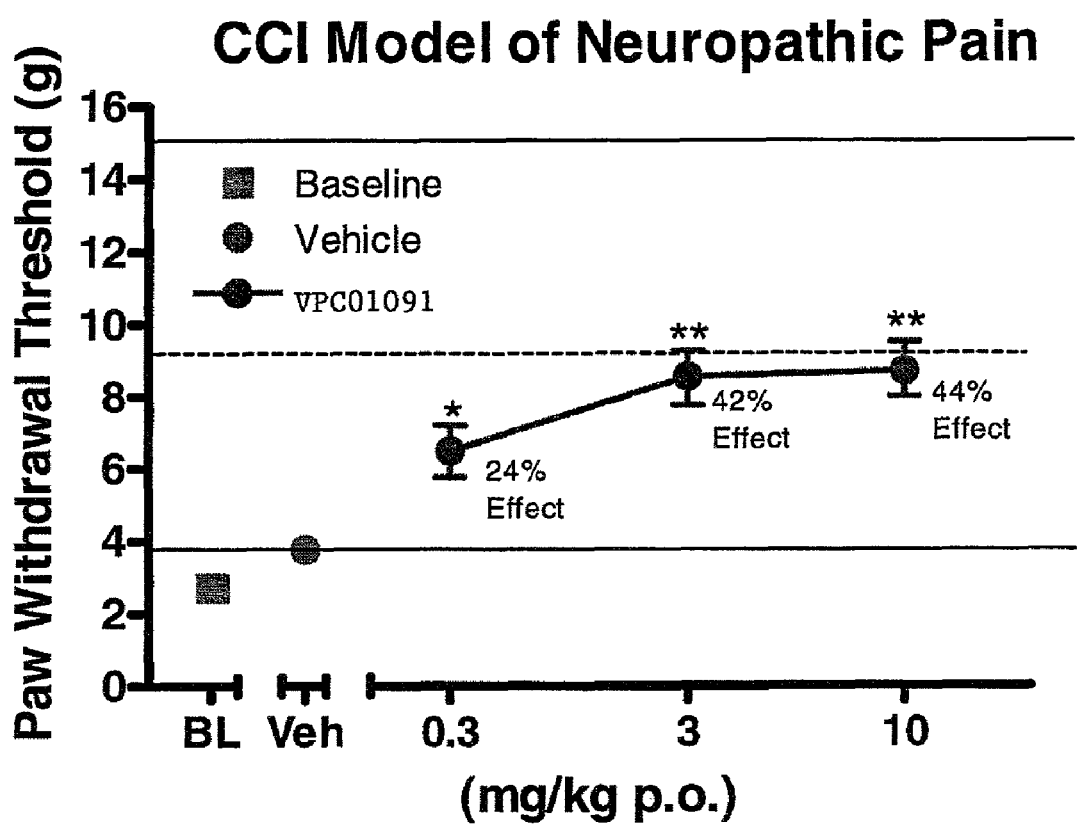
FIG. 5 is a graphical representation of the results from a sciatic nerve injury preclinical model of neuropathic pain.

The compound VPC01091-D was demonstrated to be effective at blocking mechanical allodynia associated with nerve injury in two preclinical models of neuropathic pain, sciatic nerve injury (CCI) and spinal nerve injury (SNL) models using groups of rats (7). In these models, oral treatment with VPC01091-D was started 2 weeks following nerve injury, once the pain was established. A control group received only vehicle. Following once a day dosing for 5 days, VPC01091-D (3 mg/kg, p.o.) reversed mechanical allodynia by 42±8% in the CCI model. (See FIG. 5).

VPC01091-D (3 mg/kg, p.o.) produced similar analgesic activity (50±10%) in the SNL model. Oral duloxetine, a drug approved for the treatment of neuropathic pain, produces a similar degree of analgesic efficacy in both models at a dose of 30 mg/kg, p.o.

All references cited herein are expressly incorporated herein by reference in their entirety into this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure and the claims shown below are not limited to the illustrative embodiments set forth herein.

The invention claimed is:

1. A method therapeutic treatment of neuropathic pain in a mammal, comprising administering to said mammal an effective amount of a compound having the formula:

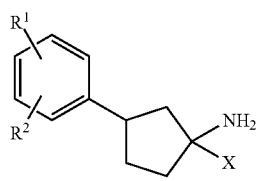

wherein X is hydroxyl, phosphate, phosphonate, or alpha-substituted phosphonate;

$R^1$ is hydrogen, halo, tri-fluoromethyl, $(C_1-C_{10})$ alkyl, $(C_1-C_{10})$ alkyl substituted with halo, hydroxy-, $(C_1-C_{10})$ alkoxy, or cyano; and $R^2$ is $(C_1-C_{20})$alkyl, cycloalkyl substituted alkyl, $(C_2-C_{20})$ alkenyl, $(C_2-C_{20})$alkynyl, aryl, alkyl substituted aryl, arylalkyl or aryl substituted arylalkyl; wherein one or more of the carbon atoms in the $R^2$ groups can be independently replaced with non-peroxide oxygen, sulfur or $NR^8$; wherein $R^8$ is hydrogen, or an $(C_1-C_{10})$ alkyl group; wherein the alkyl, alkenyl, and alkynyl groups in $R^2$ are optionally substituted with oxo; n is 2; and or a pharmaceutically acceptable salt or ester thereof.

2. The method of claim 1, wherein X is hydroxyl, phosphate, phosphonate, or alpha-substituted phosphonate;

$R^1$ is hydrogen, halo, $(C_1-C_6)$ alkyl, $(C_1-C_6)$ alkyl substituted with halo, hydroxy-, $(C_1-C_6)$ alkoxy, or cyano; and $R^2$ is alkyl, alkenyl, alkynyl, alkyl substituted aryl, alkyl substituted cycloalkyl, arylalkyl or arylalkyl substituted aryl; or a pharmaceutically acceptable salt thereof.

3. The method of claim 1, wherein $R^1$ is fluorine or chlorine.

4. The method of claim 1, wherein X is hydroxy or $OPO_3H_2$.

5. The method of claim 4, wherein X is $OPO_3H_2$.

6. The method of claim 4, wherein X is hydroxy.

7. The method of claim 1, wherein the alpha-substituted phosphonate is —$CHFPO_3H_2$, —$CF_2PO_3H_2$, —$CHOHPO_3H_2$, —C=$OPO_3H_2$ or —$OPO_2SH_2$.

8. The method of claim 7, wherein the alpha-substituted phosphonate is —$CHFPO_3H_2$, —$CF_2PO_3H_2$, —$CHOHPO_3H_2$, or —C=$OPO_3H_2$.

9. The method of claim 1, wherein $R^1$ is hydrogen.

10. The method of claim 1, wherein $R^2$ is alkyl having 5, 6, 7, or 8 carbon atoms.

11. The method of claim 10, wherein $R^2$ is heptyl, octyl, nonyl, or —O-heptyl.

12. The method of claim 11, wherein $R^2$ is n-octyl.

13. The method of claim 1, wherein the $R^2$ group is placed para to the cycloalkyl ring.

14. The method of claim 1, wherein the cycloalkyl group has the formula:

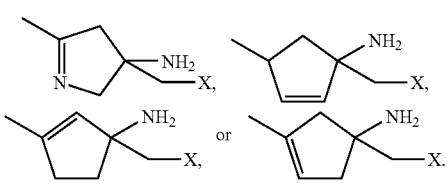
15. The method of claim 1, wherein the R¹ group is ortho or meta to R².
16. The method of claim 1, wherein the R² group is para to the benzylic cycloalkyl group.
17. The method of claim 1, wherein the compound has the formula:
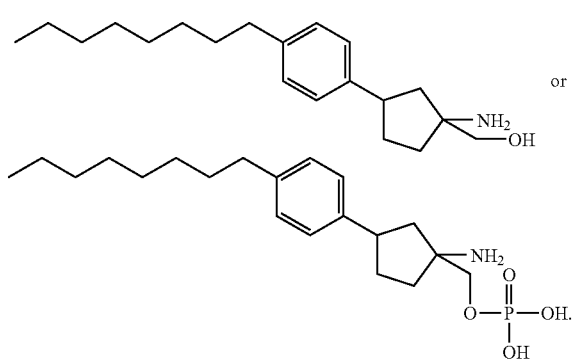
18. The method of claim 17, wherein the compound has the formula:
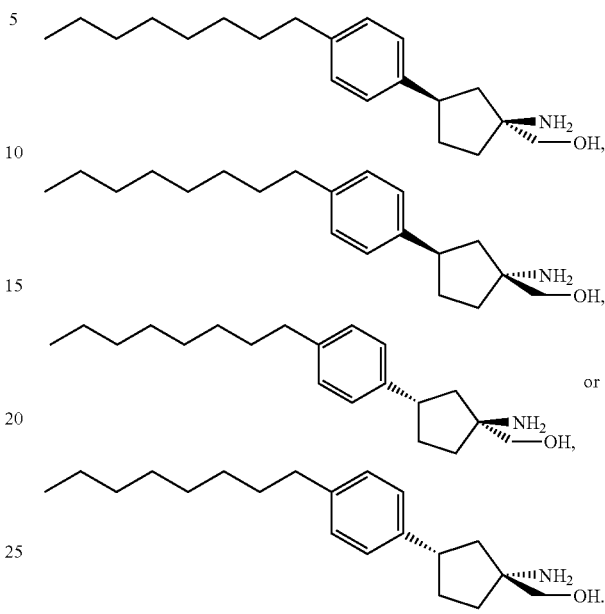
* * * * *